(12) United States Patent
Fukuzawa

(10) Patent No.: US 8,308,747 B2
(45) Date of Patent: Nov. 13, 2012

(54) PUNCTURE DEVICE

(75) Inventor: Masahiro Fukuzawa, Kyoto (JP)

(73) Assignee: Arkray, Inc., Kyoto (JP)

( * ) Notice: Subject to any disclaimer, the term of this patent is extended or adjusted under 35 U.S.C. 154(b) by 230 days.

(21) Appl. No.: 12/734,841

(22) PCT Filed: Nov. 27, 2008

(86) PCT No.: PCT/JP2008/071588
§ 371 (c)(1),
(2), (4) Date: May 27, 2010

(87) PCT Pub. No.: WO2009/069720
PCT Pub. Date: Jun. 4, 2009

(65) Prior Publication Data
US 2010/0312266 A1 Dec. 9, 2010

(30) Foreign Application Priority Data
Nov. 27, 2007 (JP) ................. 2007-306666

(51) Int. Cl.
*A61B 17/32* (2006.01)
(52) U.S. Cl. ..................................... 606/181
(58) Field of Classification Search .......... 606/181–183, 606/185; 600/564–567
See application file for complete search history.

(56) References Cited

U.S. PATENT DOCUMENTS

| | | | |
|---|---|---|---|
| 5,318,584 A | 6/1994 | Lange et al. | |
| 2003/0028126 A1* | 2/2003 | List | 600/583 |
| 2007/0055298 A1 | 3/2007 | Uehara et al. | |
| 2007/0100256 A1* | 5/2007 | Sansom | 600/583 |
| 2007/0100364 A1 | 5/2007 | Sansom | |

FOREIGN PATENT DOCUMENTS

| | | |
|---|---|---|
| CN | 1981702 A | 6/2007 |
| EP | 1 254 632 A1 | 11/2002 |
| EP | 1 669 028 A1 | 6/2006 |
| EP | 1 797 822 A1 | 6/2007 |
| JP | 07-275223 A | 10/1995 |
| JP | 2004-344291 A | 12/2004 |
| JP | 2004-344292 A | 12/2004 |
| JP | 2005-312763 A | 11/2005 |
| JP | 2006-055190 A | 3/2006 |
| JP | 2007-125382 A | 5/2007 |
| JP | 2007-125383 A | 5/2007 |

OTHER PUBLICATIONS

Office Action from Chinese Patent Office dated Aug. 24, 2011 for application No. 200880118073.3.
International Search Report mailed on Dec. 22, 2008.
Communication from European Patent Office dated Aug. 4, 2001 for application No. 08853790.7.

* cited by examiner

*Primary Examiner* — Elizabeth Houston
(74) *Attorney, Agent, or Firm* — Rader, Fishman & Grauer PLLC

(57) ABSTRACT

The present invention relates to a puncture device 1 for moving a puncture element 21 in a piercing direction N1 and for piercing a target site with the puncture element 21. The puncture device 1 is for moving a second member 42 retaining the puncture element 21 in the direction N1 and in a direction N2 by the rotational motion of a third member 40 as a first member 41 moves in the directions N1 and N2. The puncture device 1 further comprises a piercing depth adjusting mechanism 6 of adjusting a piercing depth of the puncture element 21 to the target site by regulating a rotation angle of the third member 40.

11 Claims, 12 Drawing Sheets

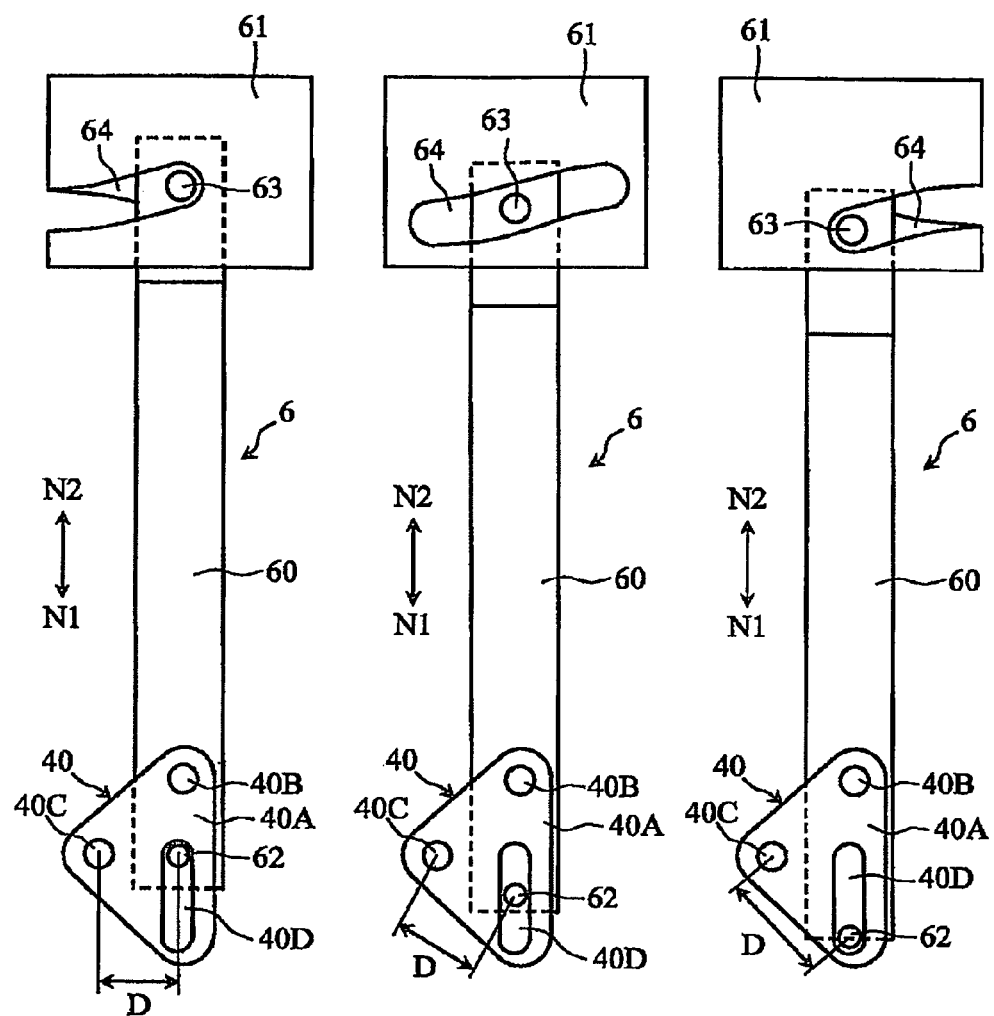

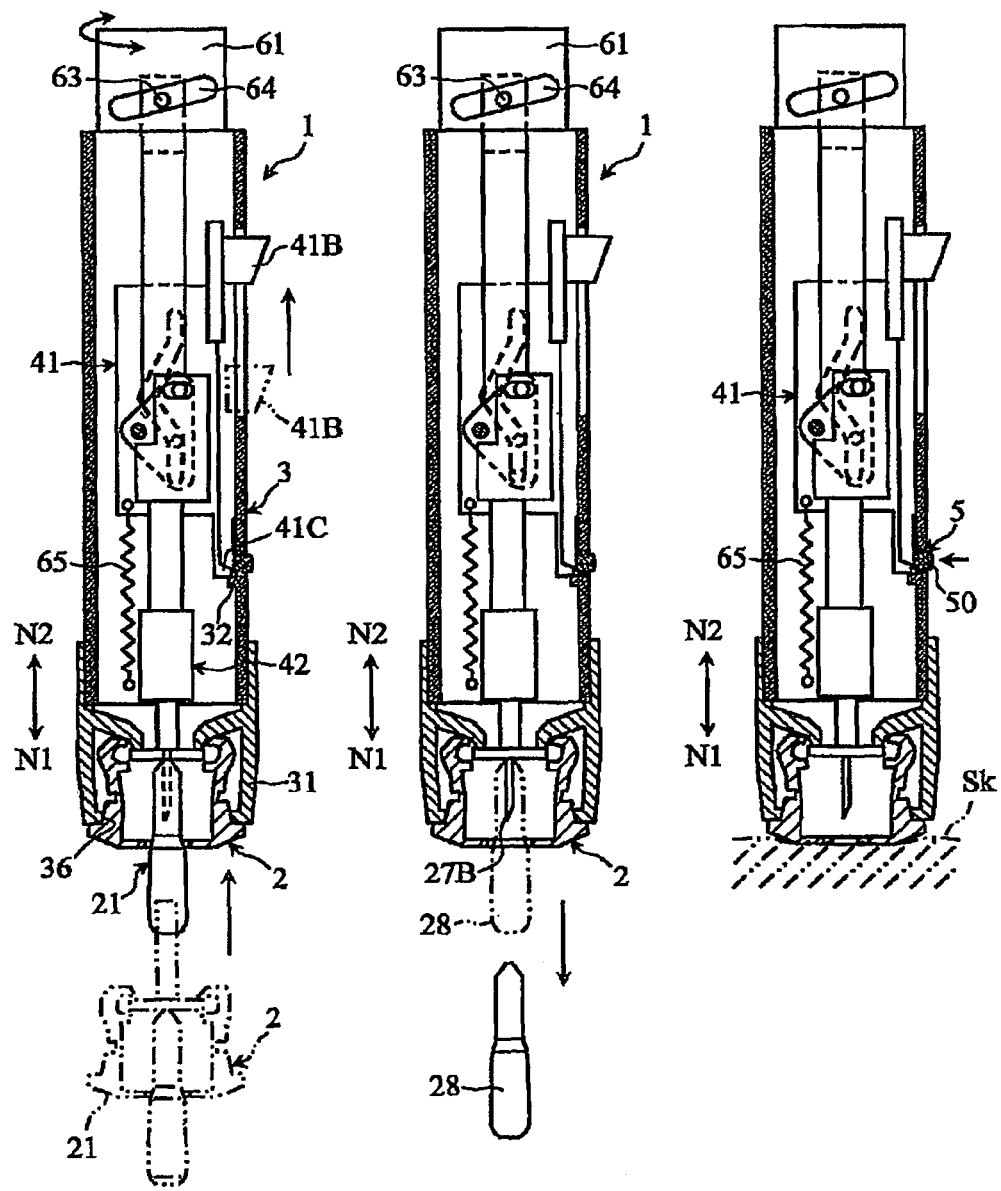

FIG.12A
FIG.12B
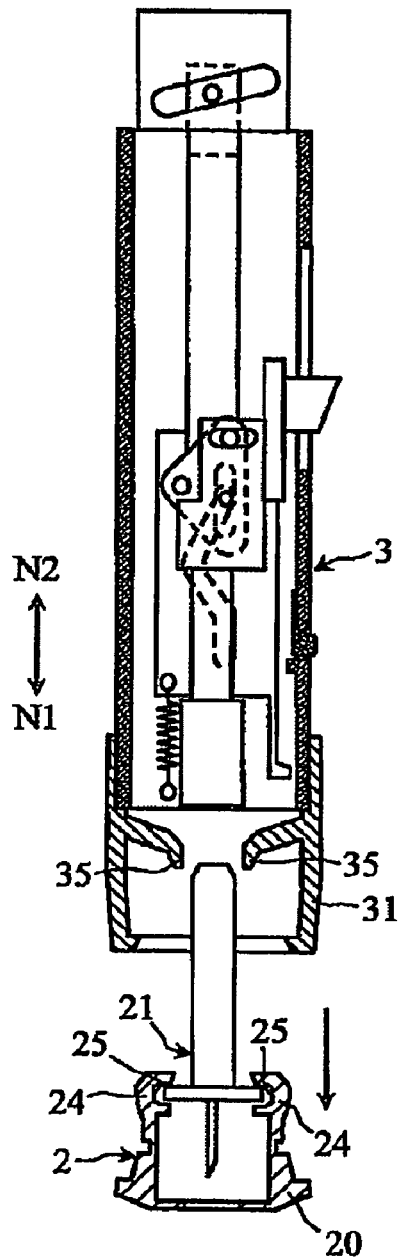
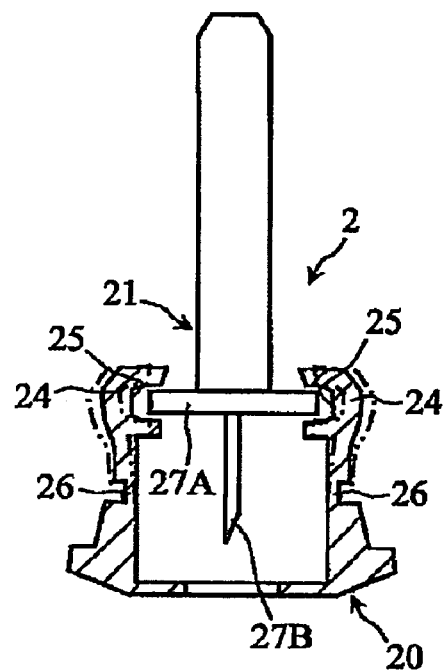

PUNCTURE DEVICE

TECHNICAL FIELD

The present invention relates to a puncture device used for piercing a skin with a puncture element like a lancet for extracting blood, other body fluids and tissues for an examination.

BACKGROUND ART

In general, a puncture device has a lancet which is moved together with a lancet holder by the elastic force of a spring to pierce a skin. As an example of such puncture device, a device which allows a user to adjust a piercing depth of a lancet relative to a skin has been proposed (see, for example, Patent Literature 1). According to such puncture device, there is a possibility that a skin is pierced plural times caused by expanding and contracting motion of the spring unless energy imparted to the lancet holder is appropriately absorbed. Moreover, even if the kinetic energy of the lancet holder can be appropriately absorbed, there is a case in which a user feels a pain when the skin is pierced because of an impact caused when the kinetic energy is absorbed. Accordingly, there has been proposed a puncture device with a cam mechanism in order to avoid plural times piercing and to reduce the pain when the skin is pierced (see, for example, Patent Literature 2).

Meanwhile, a general lancet is attached in a lancet holder, and used after a protecting cover is removed. According to such lancet, a puncture needle is exposed when the lancet is attached or discarded, so that there is a possibility that a fingertip or the like is hurt by the puncture needle. Therefore, there has been proposed a lancet, so called a safety lancet, configured to be retained in a casing so as to be bound in the casing when a user discards the lancet (see, for example, Patent Literature 3). According to such lancet, a puncture needle is surrounded by the casing when the lancet is attached, and the lancet is bound in the casing when discarded, resulting in reduction of the possibility that the puncture needle hurts the fingertip or the like when the lancet is attached or discarded.

Consequently, in order to reduce a pain when a skin is pierced and to accomplish a safeness, it is preferable to use the puncture device employing a cam mechanism, and in order to pierce the skin more safely, it is preferable to use the device in combination with the safety lancet. However, when the puncture device employs both cam mechanism and safety lancet combined together, it is difficult to further provide a mechanism of adjusting a piercing depth. For example, according to the puncture device employing a cam mechanism, as the operation of a component each configuring the cam mechanism is linked with each other, the moving distance of the lancet holder is regulated by the shape of a component or the like. Conversely, according to the safety lancet, it is necessary to regulate a positional relation between the casing and the lancet so that the lancet is appropriately bound in the casing when attached and discarded.

Patent Literature 1: Unexamined Japanese Patent Application KOKAI Publication No. 2004-344291

Patent Literature 2: Unexamined Japanese Patent Application KOKAI Publication No. 2004-344292

Patent Literature 3: Unexamined Japanese Patent Application KOKAI Publication No. 2005-312763

DISCLOSURE OF INVENTION

Problem to be Solved by the Invention

It is an object of the present invention to provide a puncture device which enables adjustment of a piercing depth to a skin while enabling piercing safely together with reduction of a pain when the skin is pierced.

Means for Solving the Problem

The present invention relates to a puncture device for moving a puncture element in a piercing direction toward a target site and for piercing the target site with the puncture element.

The puncture device of the present invention comprises a first member which is movable in the piercing direction and in an evacuating direction opposite to the piercing direction, a second member which is for retaining the puncture element, and which is movable in the piercing direction and in the evacuating direction, and a third member which is rotated as the first member moves, and is for moving the second member in the piercing direction and in the evacuating direction by a rotational motion.

The puncture device of the present invention further comprises a piercing depth adjusting mechanism of adjusting a piercing depth of the puncture element to the target site by regulating a rotation angle of the third member.

The piercing depth adjusting mechanism includes, for example, an engaging part for engaging with the third member, and a displacement member for displacing an engaging position of the engaging part in the third member. The displacement member is, for example, for displacing the engaging position of the engaging part in a link member in the piercing direction and in the evacuating direction.

The piercing depth adjusting mechanism may further include an operation member for adjusting a position of the displacement member. The piercing depth adjusting mechanism includes, for example, a protruding part provided at either one of the displacement member and the operation member, and a recess provided at the other member. Preferably, the protruding part and the recess engage with each other, and have a relative position changeable.

The operation member is, for example, for adjusting the position of the displacement member by a rotating operation. It is preferable that a moving amount of the displacement member relative to an operation amount of the operation member should be in a nonlinear relation.

The link member includes, for example, a rotating shaft with a fixed position, a movable part which is rotatable around the rotating shaft, and which causes a second member to followingly move relative to a rotational motion of the link member, and a hole for allowing positional displacement of the engaging part in the piercing direction and in the evacuating direction.

The first member comprises, for example, a recess with an inclination part inclined relative to the piercing direction and to the evacuating direction. The inclination part is a bending part comprising a first inclination part and a second inclination part which are inclined to different directions and are continuously connected to each other. Preferably, the engaging part engages with the first member at the recess.

The recess comprises, for example, a straight line part extending in the piercing direction and in the evacuating direction and connecting both ends of the bending part to each other.

The puncture device of the present invention may further comprise a housing for retaining the first member, the second member and the link member.

The first member is, for example, engaged with the housing as the first member is moved relative to the housing in the evacuating direction, and is for moving the second member in the piercing direction by releasing latching. In this case, the engaging part may move through the straight line part when the first member is relative to the housing in the evacuating direction.

Preferably, with the puncture element being retained in a casing, the puncture element is retained in the second element when attached in the housing, and conversely, when the casing is detached from the housing, the puncture element is detached from the second member and is bound by the casing so as to prevent a leading end of the puncture element from protruding from the casing.

BRIEF DESCRIPTION OF DRAWINGS

FIG. 9A to FIG. 9C are front views for explaining the piercing depth adjusting mechanism;

FIG. 10A to FIG. 10C are cross-sectional views for explaining an operation of piercing a skin using the puncture device;

FIG. 12A and FIG. 2B are cross-sectional views for explaining an operation of detaching the lancet device from the puncture device;

DESCRIPTION OF REFERENCE NUMERALS

1 Puncture device
20 Casing
21 Lancet
27B Puncture needle (puncture element)
3 Housing
40 Link member (third member)
40A Plate
40Aa Through-hole (in FIGS. 7 and 8)
40B Movable shaft (movable part) (of the link member)
40C Fixed shaft (of the link member)
40D Through-hole (hole)
41 Moving member (first member)
41A Groove (recess) (of the moving member)
41Ab Bending part (of the groove)
41Ac Straight line part (of the groove)
42 Lancet holder (second member)
6 Piercing depth adjusting mechanism
60 Control arm (displacement member) (of the piercing depth adjusting mechanism)
61 Operation cap (operation part) (of the piercing depth adjusting mechanism)
62 Engaging pin (engaging part)
63 Engaging pin (protruding part)
64 Groove (of the operation cap)
N1 Piercing direction
N2 Evacuating direction

BEST MODE FOR CARRYING OUT THE INVENTION

An explanation will be given of the present invention in detail with reference to the accompanying drawings.

Figure 1:
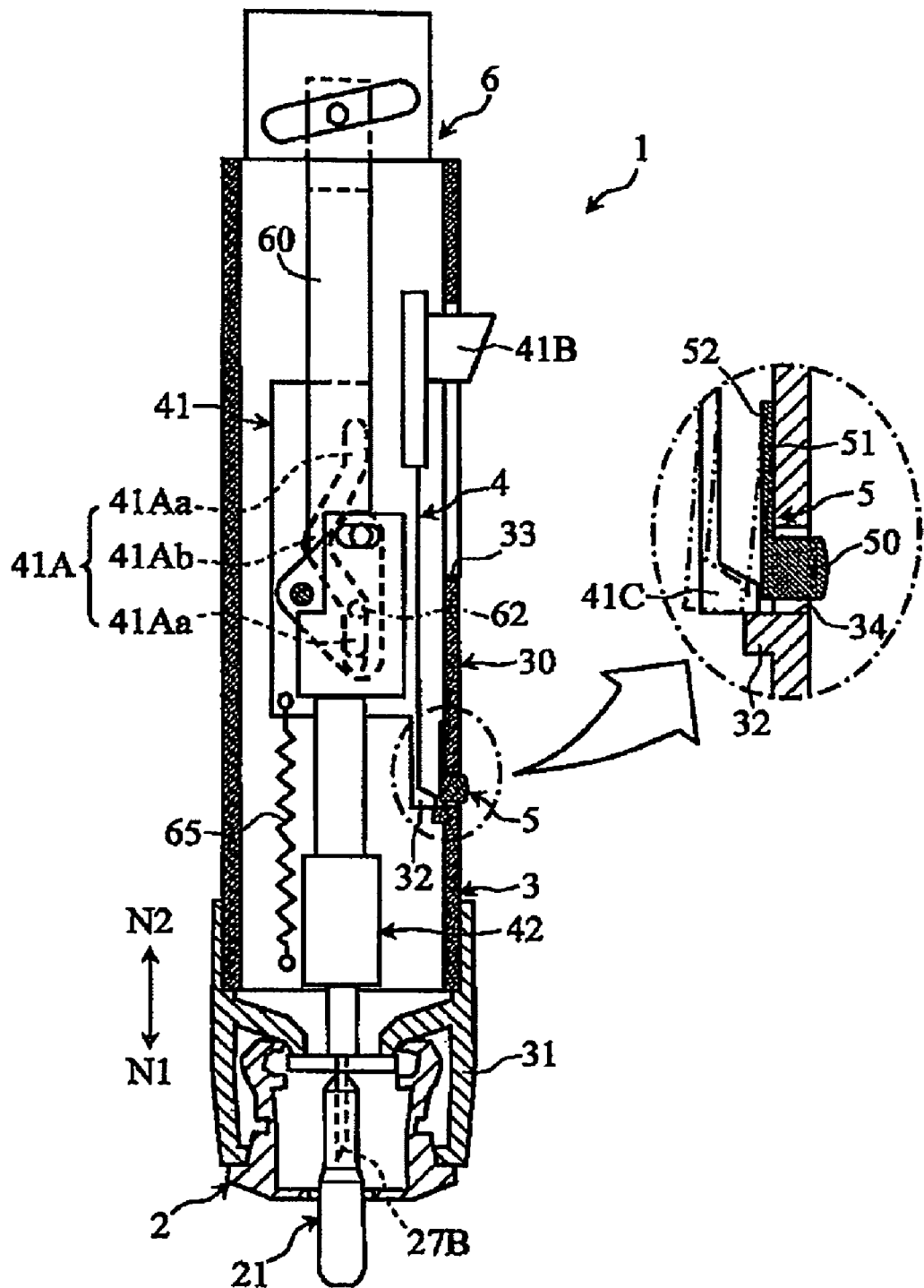
FIG. 1 is a cross-sectional view showing a lancet device attached in a puncture device according to the present invention.

A puncture device 1 shown in FIG. 1 is used for causing blood to flow out from a skin by moving a puncture needle 27B in a lancet device 2 in a piercing direction N1 to pierce the skin. The puncture device 1 comprises a housing 3, a lancet moving mechanism 4, a latch releasing member 5 and a piercing depth adjusting mechanism 6.

Figure 2A:
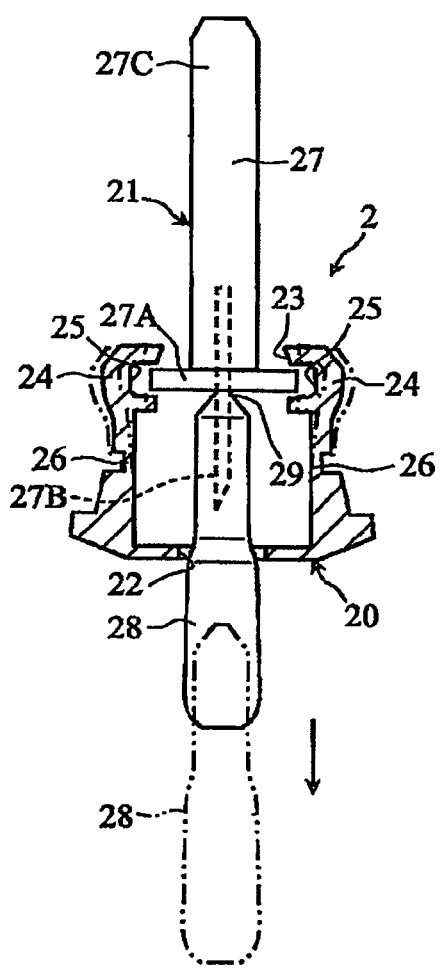
FIG. 2A and FIG. 2B are cross-sectional views for explaining the lancet device.
Figure 2B:
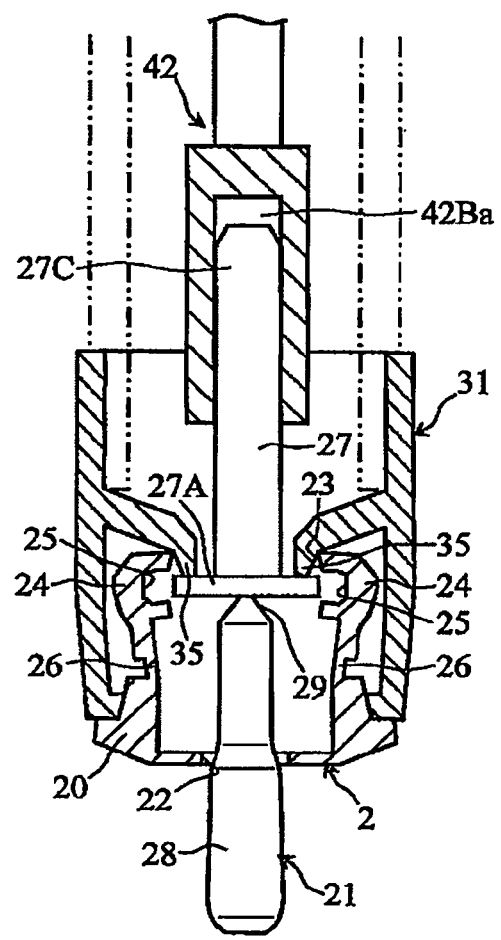

The lancet device 2 attached in the puncture device 1 is a so-called safety lancet, and comprises a casing 20 and a lancet 21 as shown in FIG. 2A and FIG. 2B.

The casing 20 is for retaining the lancet 21, and is formed in a tubular shape having openings 22 and 23. The casing 20 comprises a retaining part 24 for retaining a flange 27A of the lancet 21 to be discussed later. The retaining part 24 has a recess 25 for binding the flange 27A, and is expandable and openable in a radial direction of the casing 2 by a thin-walled part 26.

The lancet 21 is used for piercing the skin, and is retained by a lancet holder 42 in the lancet moving mechanism 4 to be discussed later. The lancet 21 comprises a lancet main body 27, a cap 28 and a brittle part 29.

The lancet main body 27 comprises an insertion end part 27C retained in a recess 42Ba of the lancet holder 42, and further comprises the flange 27A and the puncture needle 27B. The flange 27A is engaged with the retaining part 24 (the recess 25) of the casing 20, and is for preventing the lancet 21 (the lancet main body 27) from carelessly ejecting out from the casing 20. The puncture needle 27B is fixed in the lancet main body 27, and a needle tip thereof protrudes from the lancet main body 27. The cap 28 is for covering the needle tip of the puncture needle 27B, and is detachable from the lancet main body 27. When the cap 28 is detached from the lancet 21, as the needle tip of the puncture needle 27B protrudes from the lancet main body 27, it becomes in a condition that the needle tip of the puncture needle 27B is exposed. The brittle part 29 is for facilitating removal of the cap 28 from the lancet main body 27.

The above-explained lancet 21 can be formed as the puncture needle 27B is inserted therein by resin molding. Moreover, as a sterilizing process is performed on the lancet after the lancet is formed, the lancet 21 can maintain a clean condition until the cap 28 is detached and the needle tip of the puncture needle 27B is exposed.

As shown in FIG. 1, the housing 3 is for regulating a space for retaining various elements, and is formed in a cylindrical shape as a whole. The housing 3 comprises a housing main body 30 and a leading-end sleeve 31.

The housing main body 30 comprises a protruding part 32 and openings 33 and 34. The protruding part 32 is for latching a hook 41C of a moving member 41 in the lancet moving mechanism 4 to be discussed later. The opening 33 is for guiding an operation part 41B of the moving member 41. The opening 34 is for guiding a push-down part 50 of the latch releasing member 5.

As shown in FIG. 2B, the leading-end sleeve 31 is for retaining the casing 20 of the lancet device 2, and has a claw 35. The claw 35 interferes the retaining part 24 in the casing 20 when the lancet device 2 is attached in the housing 3, thereby expanding and opening the retaining part 24.

Figure 3:
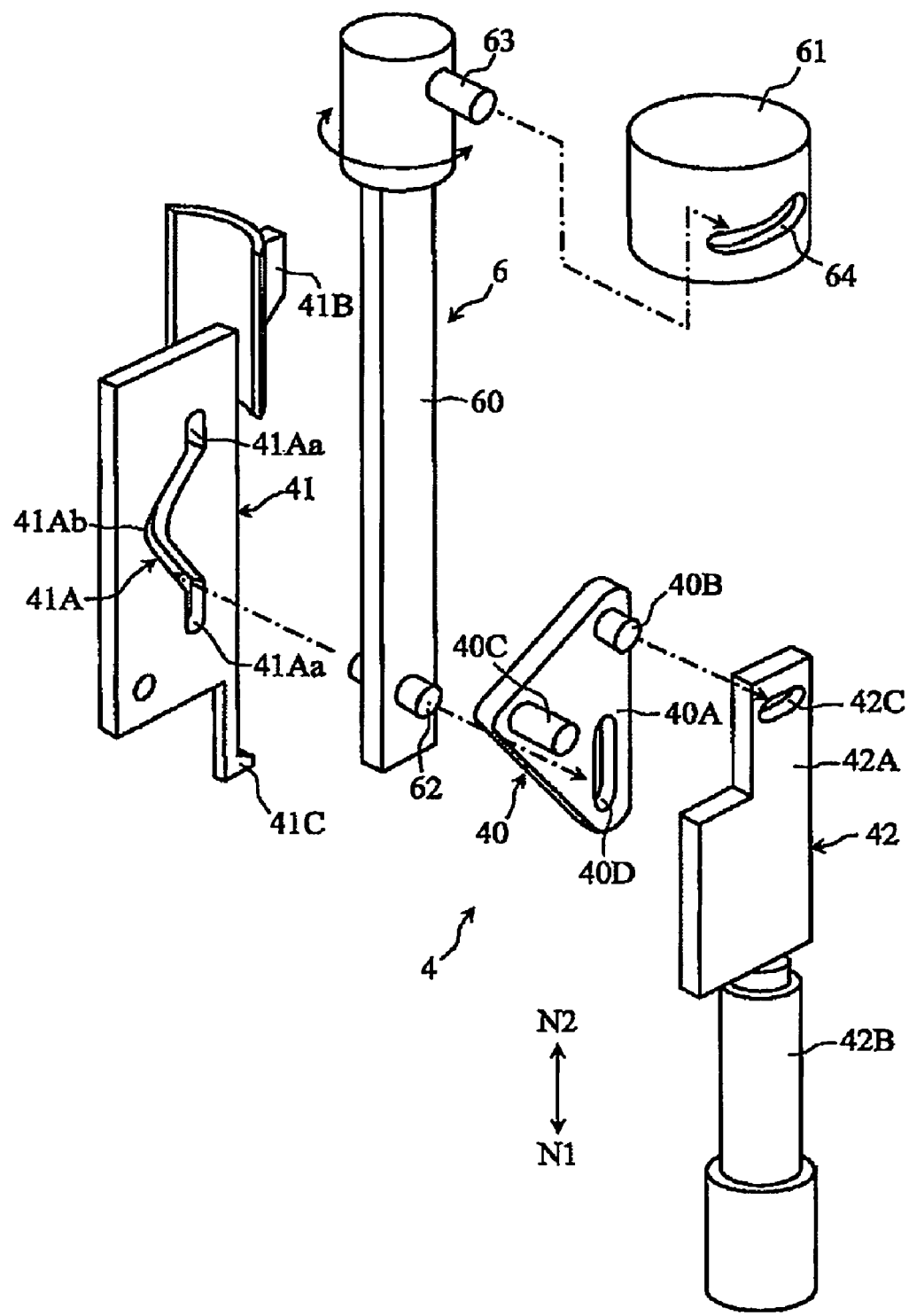
FIG. 3 is an exploded perspective view for explaining a lancet moving mechanism and a piercing depth adjusting mechanism in the puncture device shown in FIG. 1.

The lancet moving mechanism 4 employs a cam mechanism, and comprises a link member 40, the moving member 41, and the lancet holder 42 as shown in FIG. 3. The lancet moving mechanism 4 converts the translatory movement of the moving member 41 into the reciprocating motion of the lancet holder 42 through the rotational motion (rocking motion) of the link member 40.

Figure 4:
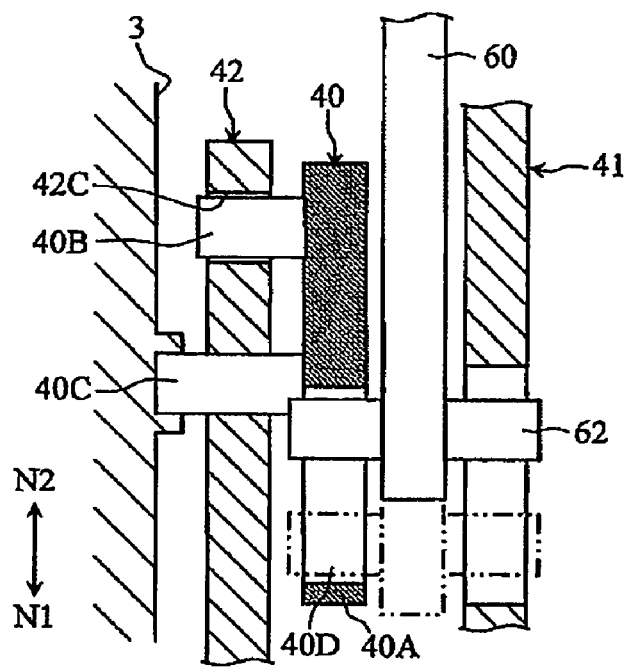
FIG. 4 is a cross-sectional view for explaining a link member in the lancet moving mechanism.
Figure 5:
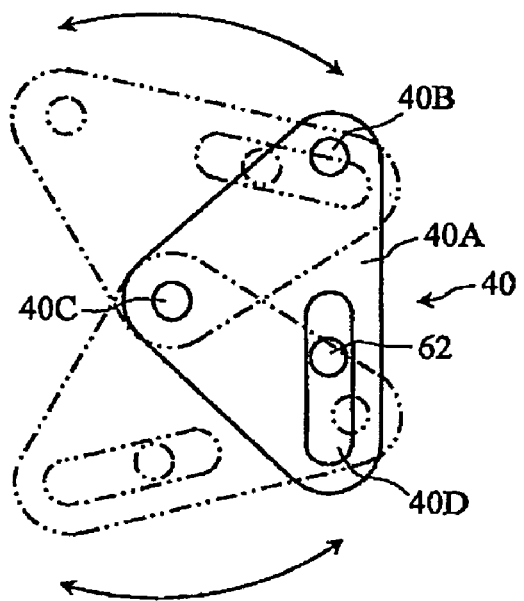
FIG. 5 is a front view for explaining the link member.

As shown in FIG. 3 to FIG. 5, the link member 40 is for interlocking the lancet holder 42 with the movement of the moving member 41 when the moving member 41 moves and for moving the lancet holder 42. The link member 40 has a plate 40A, a movable shaft 40B and a fixed shaft 40C.

The plate 40A is rotatable around the fixed shaft 40C, and is formed in a triangular shape. At respective corners of the plate 40A, the movable shaft 40B and the fixed shaft 40C are fixed while at the same time, a through-hole 40D is formed. The through-hole 40D is for engaging with an engaging pin 62 provided at a control arm 60 to be discussed later while allowing the engaging pin 62 to move.

The movable shaft 40B is for moving the lancet holder 42 in the direction N1 and a direction N2 when the plate 40A rotates, and is engaged with a through-hole 42C of the lancet holder 42. Moreover, the movable shaft 40B is so fixed as not to be rotatable in an axial direction at the corner of the plate 40A, and a distance to the fixed shaft 40C is fixed.

The fixed shaft 40C is for fixing the link member 40 rotatable relative to the housing 3. The fixed shaft 40C is so fixed as not to be rotatable in the axial direction at the corner of the plate 40A while at the same time being fixed rotatable in the axial direction relative to the housing 3.

Figure 6:
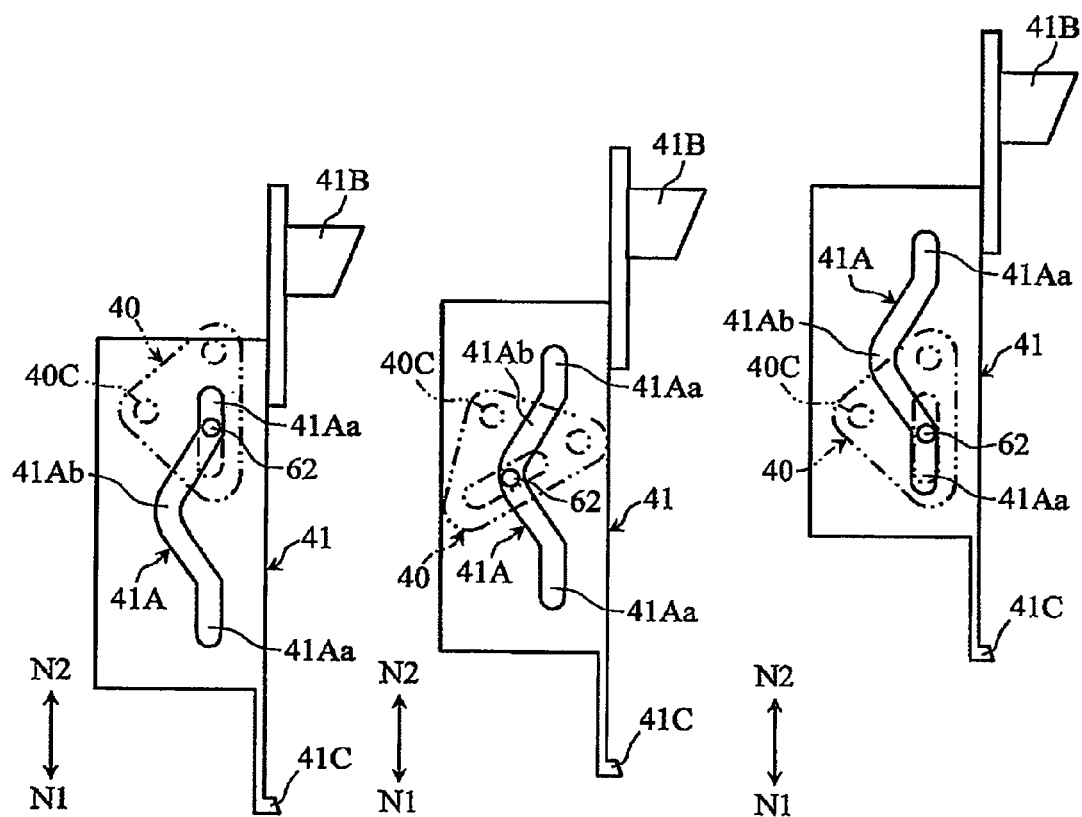
FIG. 6A to FIG. 6C are front views for explaining a relation between the link member and a moving member.

As shown in FIG. 1, FIG. 3 and FIG. 6, the moving member 41 is movable relative to the housing 3 in the directions N1 and N2, and is connected to the housing 3 through a coil spring 65. The moving member 41 comprises a groove 41A, the operation part 41B and the hook 41C.

The groove 41A is for allowing the engaging pin 62 to be discussed later to move, and has a straight line part 41Aa and a bending part 41Ab. The straight line part 41Aa extends in the directions N1 and N2 while the bending part 41Ab is offset relative to the straight line part 41Aa as a whole. Accordingly, the link member 40 (the plate 40A) is rotated (rocked) when the engaging pin 62 moves through the bending part 41Ab.

The operation part 41B is used when the moving member 41 is moved by hand. The operation part 41B has a portion thereof protruding toward the exterior through the opening 33 of the housing 3, while at the same time, is guided by the opening 33 to move in the directions N1 and N2.

The hook 41C is for engaging with the protruding part 32 of the housing 32 (the housing main body 30), thereby latching the moving member 41 to the housing 3.

Figure 7:
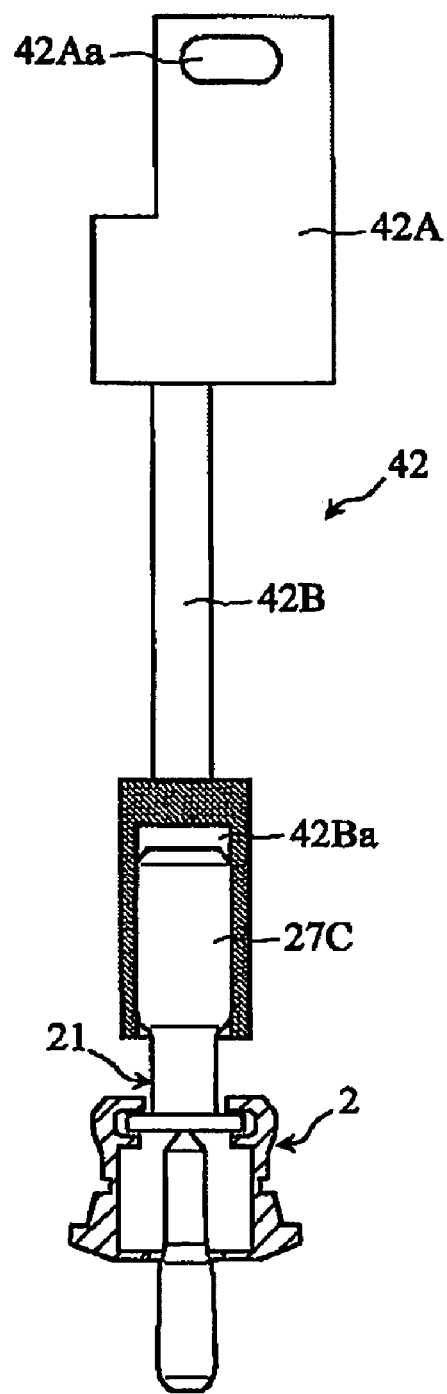
FIG. 7 is a front view for explaining the lancet holder with a portion thereof shown in section.

As shown in FIG. 7 and FIG. 8, the lancet holder 42 is for retaining the lancet 21 in the lancet device 2, and for moving the lancet 21. The lancet holder 42 comprises a plate 42A and a rod 42B.

The plate 42A is moved as the movable shaft 40B of the link member 40 rotates (rocks), and has the through-hole 42Aa. The through-hole 42Aa is engaged with the movable shaft 40B, and is formed in a long hole extending in a direction perpendicular to the directions N1 and N2 so as to allow the plate 42A to move in the directions N1 and N2 when the movable shaft 40B is rotated (rocked).

The rod 42B has the recess 42Ba for retaining the lancet 21. The recess 42Ba has an internal diameter substantially equal to an external diameter of the insertion end part 27C of the lancet 21 (the lancet main body 27).

As shown in FIG. 1, the latch releasing member 5 is for releasing latching of the moving member 41 from the housing 3 (the protruding part 32), and has the push-down part 50 and an elastic part 51. The push-down part 50 is exposed on the outer surface of the housing 3 and can wobble in a radial direction of the housing 3. The elastic part 51 has moderate elasticity, and extends from the push-down part 50, and is fixed to the housing 3 at an end part 52.

In the above-explained latch releasing member 5, when the push-down part 50 is pushed down, the push-down part 50 acts on the hook 41C of the moving member 41, thereby releasing engagement of the hook 41C with the protruding part 32 of the housing 3.

Figure 11A:
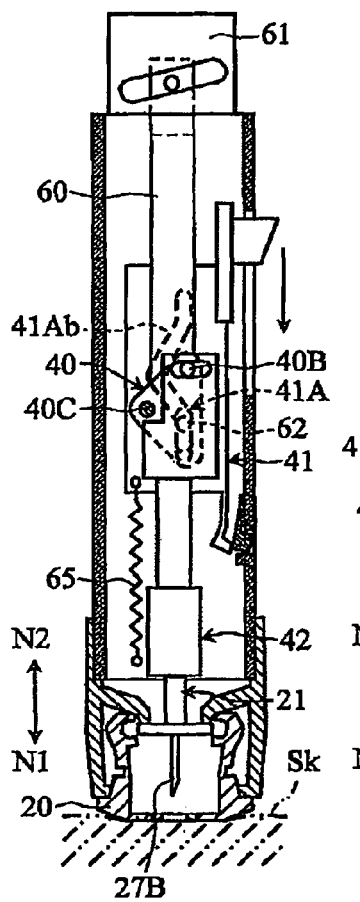
FIG. 11A to FIG. 11C are cross-sectional views for explaining the operation of piercing the skin using the puncture device.
Figure 11B:
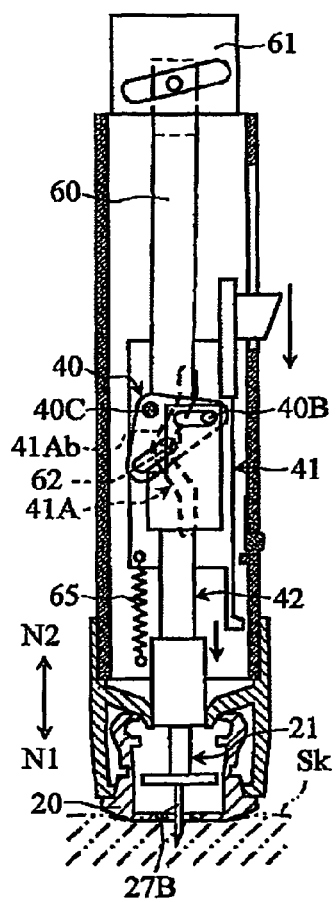

As shown in FIG. 3 and FIG. 9A, the piercing depth adjusting mechanism 6 is for adjusting a protruding amount of the puncture needle 27B from the casing 20 of the lancet device 2 when a skin is pierced, i.e., an insertion depth of the puncture needle 27B relative to a skin Sk (see, FIG. 11B). The piercing depth adjusting mechanism 6 comprises the control arm 60 and an operation cap 61.

The control arm 60 has the engaging pin 62 and an engaging pin 63 respectively provided at both ends. The engaging pin 62 is for rocking (rotating) the plate 40A when moving through the bending part 41Ab of the groove 41A, and engages with the through-hole 40D of the plate 40A of the link member 40 and the groove 41A of the moving member 41. Meanwhile, the engaging pin 63 is for engaging with a groove 64 of the operation cap 61, and acts as a supporting point for wobbling the control arm 60 when the engaging pin 62 moves through the bending part 41Ab.

The operation cap 61 is for adjusting positions of the control arm 60 in the directions N1 and N2, and is formed in a hollow cylindrical shape. The operation cap 61 is rotatable, and has the groove 64 for engaging with the engaging pin 63. The groove 64 is inclined to the direction perpendicular to the directions N1 and N2 (a horizontal direction in the figure), and is for displacing positions of the control arm 60 in the directions N1 and N2. That is, as shown in FIG. 9A to FIG. 9C, as the operation cap 61 is rotated, the engaging position with the engaging pin 63 changes, thereby displacing the control arm 60 in the directions N1 and N2. The shape of the groove 64 can be a shape such that the moving distance of the engaging pin 63 linearly changes relative to a rotation angle of the operation cap 61, or can be a shape such that the moving distance changes nonlinearly. When the groove 64 is formed in such a shape that the moving distance of the engaging pin changes nonlinearly relative to the rotation angle of the operation cap 61, the moving distance of the engaging pin 63 relative to the rotation angle of the operation cap 61 may be set to be smaller within the range of a general piercing depth. For example, within the smaller range of a piercing depth, the moving distance of the engaging pin 63 relative to the rotation angle of the operation cap 61 may be set to be smaller. Meanwhile, within the larger range of a piercing depth, the moving distance of the engaging pin 63 relative to the rotation angle of the operation cap 61 may be set to be larger. According to such configuration, when the range of a piercing depth is small, that is, when a small amount of blood is extracted, a piercing depth can be finely adjusted, which results in improvement of the usability of the puncture device.

A distance D between the engaging pin 62 and the fixed shaft 40C of the link member 40 changes in accordance with a position of the engaging pin 62 in the groove 40D. Accordingly, by rotating the operation cap 61 and changing positions of the control arm 60 in the directions N1 and N2, it becomes possible to change the distance D between the engaging pin 62 and the fixed shaft 40C.

The link member 40 is for converting the translatory movement of the moving member 41 into the reciprocating motion of the lancet holder 42. Accordingly, under a condition in which the stroke of the moving member 41 remains same, the distance D between the engaging pin 62 and the fixed shaft 40C of the link member 40 affects a rotation angle of the link member 40 when the engaging pin 62 moves through the groove 41A (see, FIG. 6A to FIG. 6C). That is, the rotation angle of the link member 40 becomes large when the distance D is small, and in contrast, the rotation angle becomes small when the distance D is large.

Figure 8A:
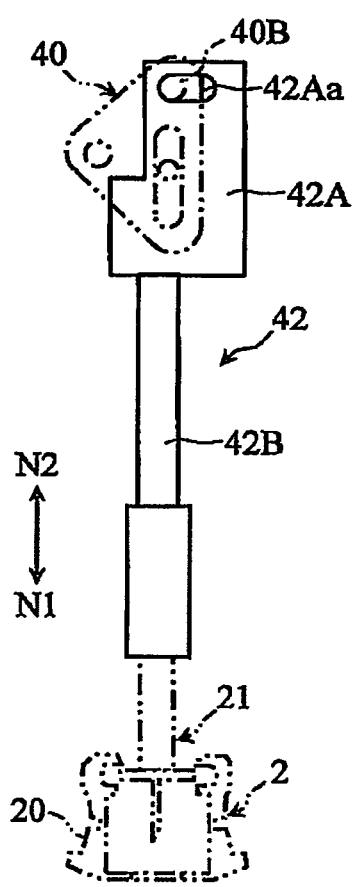
FIG. 8A to FIG. 8C are front views for explaining a relation between the link member and the lancet holder.
Figure 8B:
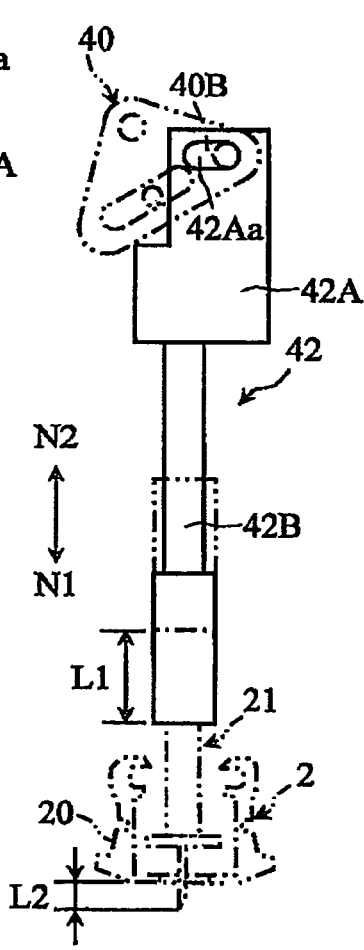
Figure 8C:
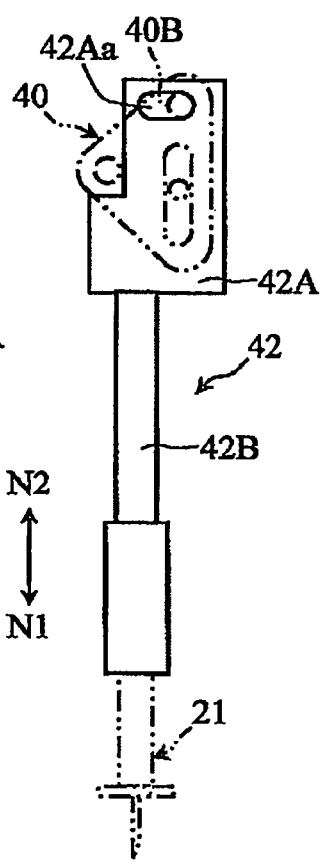

Meanwhile, the lancet holder 42 is connected to the link member 40 through the movable shaft 40B, and a position of the lancet holder 42 is regulated by a position of the movable shaft 40B (see, FIG. 8A to FIG. 8C). Accordingly, when the rotation angle of the link member 40 is large, positional displacement of the movable shaft 40B in the directions N1 and N2 becomes large, thereby to increase a stroke L1 of the lancet holder 42. Consequently, the stroke of the lancet 21 retained by the lancet holder 42 becomes large and a maximum protruding amount L2 of the puncture needle 27B from the casing 20 and eventually, a piercing depth of the puncture needle 27B to the skin become large. On the other hand, when a rotation angle of a link member 40 is small, the stroke L1 of the lancet holder 42 becomes small, which leads the maximum protruding amount L2 (a piercing depth) of the puncture needle 27B from the casing 20 to be small. Consequently, in the puncture device 1, a piercing depth of the puncture needle 27B relative to the skin can be adjusted by rotating the operation cap 61.

It is explained below how to use the puncture device 1 and an operating principle thereof.

As shown in FIG. 10A, when a skin is pierced with the puncture device 1, first, the lancet 21 of the lancet device 2 is retained in the lancet holder 42 and the hook 41C of the moving member 41 is caused to engage with the protruding part 32 of the housing 3.

The lancet 21 can be retained in the lancet holder 42 as the lancet device 2 is inserted from the opening 35 of the leading-end sleeve 31. When the lancet device 2 is inserted from the opening 35 of the leading-end sleeve 31, the insertion end part 27C of the lancet 21 is fitted into the recess 42Ba of the lancet holder 42 as shown in FIG. 7. At this time, as shown in FIG. 2B, the claw 35 of the leading-end sleeve 31 acts on the retaining part 24 of the casing 20 of the lancet device 2. Accordingly, the retaining part 24 expands in the radial direction, engagement of the retaining part 24 with the flange 27A of the lancet 21 is released, which leads the lancet 21 to be free relative to the casing 20.

Meanwhile, as shown in FIG. 10A, the hook 41C of the moving member 41 can be engaged with the protruding part 32 of the housing 3 as the operation part 41B of the moving member 41 is moved in the direction N2. When the operation part 41B is moved by a predetermined distance in the direction N2, the hook 41C is engaged with the protruding part 32 and the coil spring 65 is stretched.

Next, as shown in FIG. 10B, the cap 28 of the lancet 2 is detached. The cap 28 can be detached by twisting and moving the cap 28 in the direction N1.

When a piercing depth of the puncture needle 27B to the skin is to be adjusted, it is appropriate if the operation cap 61 is rotated before the latching condition of the hook 41C with the protruding part 32 is released. Accordingly, as explained above with reference to FIG. 9A to FIG. 9C, a position of the engaging pin 62 in the through-hole 40D of the link member 40 is changed, allowing the stroke L1 of the lancet holder 42 and eventually, the maximum protruding amount L2 of the puncture needle 27B from the casing 20 of the lancet device 2 (a piercing depth of the puncture needle 27B to the skin in the lancet 21) to be adjusted (see, FIG. 8B). As explained above, in the puncture device 1, a piercing depth of the puncture needle 27B to the skin Sk can be performed through a simple operation like rotating the operation cap 61.

Next, as shown in FIG. 10C, with an end face of the lancet device 2 (the casing 20) being pressed against the skin Sk, the skin is pierced as the push-down part 50 of the latch releasing member 5 is pushed down. As shown in FIG. 1 and FIG. 11A, when the push-down part 50 is pushed down, as the push-down part 50 is displaced inwardly, the hook 41C is moved inwardly by the push-down part 50. Accordingly, latching of the hook 41C with the protruding part 32 is released.

Figure 11C:
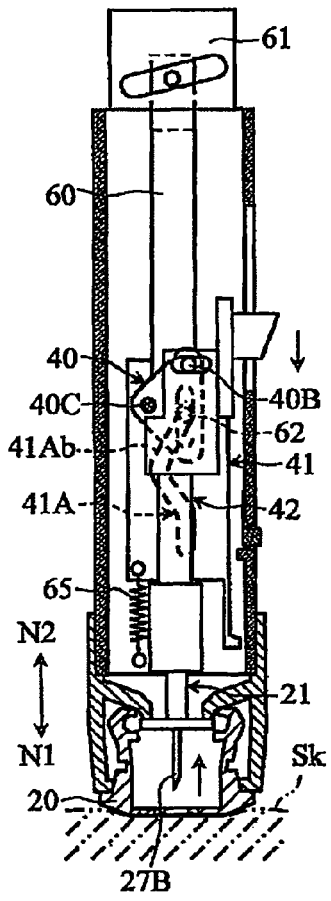

In the meantime, because the moving member 41 is connected to the coil spring 65 and the coil spring 65 is stretched, as shown in FIGS. 11A to 11C, the moving member 41 moves in the direction N1 by the elastic force of the coil spring 65. At this time, as the engaging pin 62 of the control arm 60 moves through the bending part 41Ab of the groove 41A of the moving member 41, the link member 40 rotates (rocks) around the fixed shaft 40C. On the other hand, as the link member 40 rotates (rocks), the lancet holder 42 is moved in the direction N1 by the movable shaft 40B, and then moved in the direction N2 (see, FIG. 8A to FIG. 8C). At this time, because the lancet 21 is retained in the lancet holder 42, the lancet 21 also moves in the direction N1, and then moves in the direction N2.

As the puncture needle 27B is exposed from the lancet 21, when the lancet 21 is moved in the direction N1, the puncture needle 27B protrudes from the casing 20, and pierces the skin Sk. Conversely, when the lancet 21 moves in the direction N2, the puncture needle 27B is pulled out from the skin Sk, and the piercing operation completes. In this manner, piercing of the skin Sk by the lancet 21 and pulling out of the puncture needle 27B are performed together with the movement of the moving member 41 in the direction N1. Accordingly, it is possible not only to reduce a pain as a time while the puncture needle 27B is piercing the skin Sk is reduced, but also to accomplish a safeness as the puncture needle 27B is retained in the casing 20 after piercing the skin. Moreover, as the puncture device 1 employs the cam mechanism, the puncture needle 27B will not move in the direction N1 again after being pulled out from the skin Sk, thereby avoiding plural times piercing of the skin.

When piercing of the skin Sk by the lancet 21 completes, as shown in FIG. 12A, the lancet 2 is detached from the housing 3 (the leading-end sleeve 31). The lancet device 2 can be detached as the lancet device 2 is moved relative to the housing 3 in the direction N1.

When the lancet device 2 is moved relative to the housing 3 in the direction N1, the action of the claw 35 of the leading-end sleeve 3 on the retaining part 24 of the casing 20 is released. As a result, as shown in FIG. 12B, the retaining part 24 is displaced toward the internal side of the radial direction, which leads the flange 27A of the lancet 21 to engage with the recess 25. Accordingly, the lancet 21 is fixed in the casing 20, so that it becomes possible to prevent the puncture needle 27B from protruding from the casing 20, and the lancet device 2 can be detached and discarded safely and hygienically.

As explained above, the puncture device 1 can further adjust a piercing depth by regulating the rotation angle of the link member 40 by the cam mechanism without providing a mechanism of adjusting a piercing depth in the lancet device 2. Accordingly, a positional relation between the lancet 21 and the casing 20 can be same in both cases in which the lancet 21 is attached in the lancet holder 42, and in which the lancet 21 is detached from the lancet holder 42. Consequently, even if the puncture device 1 employing the cam mechanism uses the so-called safety lancet, it is possible to appropriately secure a function as the safety lancet, and to pierce a skin safely and hygienically.

It is appropriate if the puncture device according to the present invention employs a configuration which can adjust a piercing depth by adjusting the rotation angle of the link member, and such a configuration is not limited to the foregoing embodiment. For example, the puncture device of the present invention can employ a configuration that a recess like a groove is provided in a control arm, and as a connecting element like a pin fixed to a link member, or a connecting element like a pin to be engaged with the link member engages with the recess, the rotation angle of the link member can be adjusted in accordance with a position of the control arm. Moreover, the rotation angle of the link member (the distance between the fixed shaft and the engaging pin) may be regulated by displacing the engaging position of the engaging pin relative to the link member in a direction inclined to the piercing direction N1 and the evacuating direction N2.

Figures 13A, 13B, 13C:
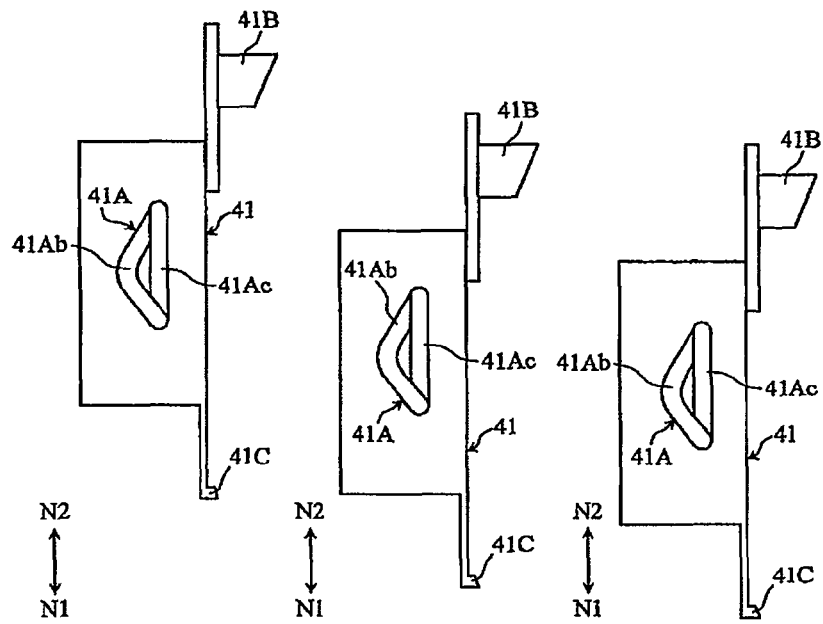
FIG. 13A to FIG. 13C are front views showing another example of the moving member in the puncture device of the present invention.

As shown in FIG. 13A to FIG. 13C, the groove 41A of the moving member 41 may have the bending part 41Ab with both ends thereof being connected by a straight line part Ac extending in the directions N1 and N2.

Figure 14:
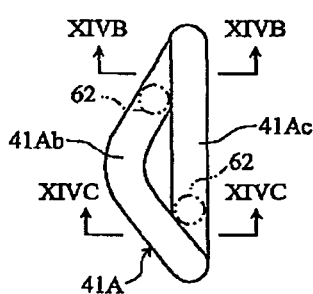
FIG. 14A is a front view showing a groove in the moving member.
FIG. 14B is a cross-sectional view along a line XIVB-XIVB in FIG. 14A.
FIG. 14C is a cross-sectional view along a line XIVC-XIVC in FIG. 14A.
Figure 14B:
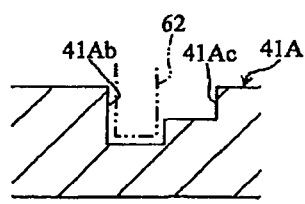
Figure 14C:
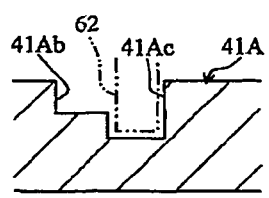

As shown in FIG. 14A and FIG. 14C, steps are provided between an upper end of the straight line part 41Ac and the bending part 41Ab, and the upper end of the straight line 41Ac and the bending part 41Ab. Accordingly, the engaging pin 62 is prohibited from moving from an upper end of the bending part 41Ab to the upper end of the straight line part 41Ac in the groove 41A, or from a lower end of the straight line part 41Ac to a lower end of the bending part 41Ab. As a result, the engaging pin 62 moves through the groove 41A in a counterclockwise direction in the figures. Moreover, the engaging pin 62 moves through the straight line part 41Ac when the moving member 41 is moved relative to the housing 3 in the evacuating direction N2 (when the moving member 41 is latched to the housing 3).

According to such configuration, when the moving member 41 is latched to the housing, the lancet holder 42 is prohibited from moving in the piercing direction N1 or in the evacuating direction N2 relative to the housing 3. Accordingly, even if the lancet holder 42 is engaged with the housing 3 after the lancet 27 (the puncture needle 27B) is attached in the lancet holder 42, a position of the lancet 27 (the puncture needle 27B) does not move in the piercing direction N1 or in the evacuating direction N2. As a result, it becomes possible to prevent the lancet 27 (the puncture needle 27B) from protruding from the casing 20 when the hook 41C of the moving member 41 is engaged with (latched to) the protruding part 32 of the housing 3, resulting in reduction of the possibility that a user is subjected to a danger by the lancet 27 (the puncture needle 27B).

The present invention can be further applicable to a puncture device employing a lancet other than the safety lancet.

The invention claimed is:

1. A puncture device for moving a puncture element in a piercing direction toward a target site and for piercing the target site with the puncture element, the puncture device comprising:
    a first member which is movable in the piercing direction and in an evacuating direction opposite to the piercing direction;
    a second member which is for retaining the puncture element, and which is movable in the piercing direction and in the evacuating direction; and
    a third member which is rotated as the first member moves, and is for moving the second member in the piercing direction and in the evacuating direction by a rotational motion, the puncture device further comprising:
    a piercing depth adjusting mechanism of adjusting a piercing depth of the puncture element to the target site by regulating a rotation angle of the third member,
    wherein the piercing depth adjusting mechanism includes an engaging part for engaging with the third member, and includes a displacement member for displacing an engaging position of the engaging part in the third member;
    the first member includes a recess with an inclination part inclined relative to the piercing direction and to the evacuating direction; and
    the engaging part engages with the first member at the recess.

2. A puncture device for moving a puncture element in a piercing direction toward a target site and for piercing the target site with the puncture element, the puncture device comprising:
    a first member which is movable in the piercing direction and in an evacuating direction opposite to the piercing direction;
    a second member which is for retaining the puncture element, and which is movable in the piercing direction and in the evacuating direction; and
    a third member which is rotated as the first member moves, and is for moving the second member in the piercing direction and in the evacuating direction by a rotational motion, the puncture device further comprising:
    a piercing depth adjusting mechanism of adjusting a piercing depth of the puncture element to the target site by regulating a rotation angle of the third member,
    wherein the piercing depth adjusting mechanism includes an engaging part for engaging with the third member, and includes a displacement member for displacing an engaging position of the engaging part in the third member; and
    the third member includes a rotating shaft with a fixed position, a movable part which is rotatable around the rotating shaft, and which causes a second member to followingly move relative to a rotational motion of the third member, and a hole for allowing positional displacement of the engaging part.

3. The puncture device according to claim 1, wherein the piercing depth adjusting mechanism further includes an operation member for adjusting a position of the displacement member.

4. The puncture device according to claim 3, wherein the piercing depth adjusting mechanism includes a protruding part provided at either one of the displacement member and the operation member, and a recess provided at the other member, and the protruding part and the recess engage with each other, and has a relative position changeable.

5. The puncture device according to claim 3, wherein the operation member is for adjusting the position of the displacement member by a rotating operation.

6. The puncture device according to claim 3, wherein a moving amount of the displacement member relative to an operation amount of the operation member is in a nonlinear relation.

7. The puncture device according to claim 1, wherein the displacement member is for displacing an engaging position of the engaging part in the third member in the piercing direction and in the evacuating direction.

8. The puncture device according to claim 1, wherein the third member includes a rotating shaft with a fixed position, a movable part which is rotatable around the rotating shaft, and which causes the second member to followingly move relative to the rotational motion of the third member, and a hole for allowing positional displacement of the engaging part.

9. The puncture device according to claim 1, wherein
the inclination part is a bending part including the first inclination part and the second inclination part which are inclined to different directions and are continuously connected to each other, and
the recess further includes a straight line part extending in the piercing direction and in the evacuating direction and connecting both ends of the bending part to each other.

10. The puncture device according to claim 9, further comprising a housing for retaining from the first member to the third member, wherein
the first member is engaged with the housing as the first member is moved relative to the housing in the evacuating direction, and is for moving the second member in the piercing direction by releasing latching, and
the engaging part moves through the straight line part when the first member is moved relative to the housing in the evacuating direction.

11. The puncture device according to claim 1, further comprising a housing for retaining the first member, the second member and the third member, wherein
with the puncture element being retained in a casing, the puncture element is retained in the second element when attached in the housing, and, when the casing is detached from the housing, the puncture element is detached from the second member and is bound in the casing so as to prevent a leading end of the puncture element from protruding from the casing.

* * * * *